US006242437B1

(12) United States Patent
Kobayashi et al.

(10) Patent No.: US 6,242,437 B1
(45) Date of Patent: Jun. 5, 2001

(54) CEPHEM DERIVATIVES

(75) Inventors: Kazuko Kobayashi; Eijirou Umemura; Kunio Atsumi; Takashi Ida, all of Yokohama (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 09/319,437

(22) PCT Filed: Dec. 8, 1997

(86) PCT No.: PCT/JP97/04489

§ 371 Date: Jun. 7, 1999

§ 102(e) Date: Jun. 7, 1999

(87) PCT Pub. No.: WO98/25935

PCT Pub. Date: Jun. 18, 1998

(30) Foreign Application Priority Data

Dec. 9, 1996 (JP) .................................... 8-328761

(51) Int. Cl.$^7$ ...................... A61K 31/546; C07D 519/06; A61P 31/04

(52) U.S. Cl. ........................... 514/205; 540/227; 544/346

(58) Field of Search .............................. 540/227; 514/205

(56) References Cited

U.S. PATENT DOCUMENTS 5,663,162   9/1997  Atsumi et al. ...................... 514/202

FOREIGN PATENT DOCUMENTS

| 0723966 | 7/1996 | (EP) . |
| 8-245637 | 9/1996 | (JP) . |
| 8-311071 | 11/1996 | (JP) . |
| 9507912 | 3/1995 | (WO) . |
| 96/37499 | 11/1996 | (WO) . |
| 98/22469 | * 5/1998 | (WO) . |

OTHER PUBLICATIONS

Abstract of JP 8–245637 (Sep. 24, 1996).
Abstract of JP 8–311071 (Nov. 26, 1996).
Chemical Abstracts, vol. 126, No. 2, Jan. 13, 1997 Columbus, Ohio, US; abstract No. 18715, Umemura E. et al.: "Preparation of heterocyclyliumylcephemcarboxylate inner salts" XP002132267 *abstract*.

* cited by examiner

Primary Examiner—Mark L. Berch
(74) Attorney, Agent, or Firm—Wenderoth, Lind & Ponack, L.L.P.

(57) ABSTRACT

A compound represented by the following formula (I) is disclosed. This compound has potent antimicrobial activity against a wide spectrum of bacteria from Gram-positive bacteria to Grame-negative bacteria including β-lactamase producing bacteria. In particular, it has higher antimicrobial activity against methicilline-resistant Staphylococcus aureus (MRSA), penicillin-resistant Streptococcus pneumoniae (PRSP), and imipenem-resistant Pseudomonas aeruginosa than the existing onium salt type cephem derivatives and hence is very useful as a therapeutic agent for infectious diseases derived from various pathogenic bacteria.

(I)

wherein X represents CH or N, $R^1$ represents a hydrogen atom, substituted or unsubstituted $C_{1-6}$ alkyl, $C_{2-6}$ alkenyl, $C_{2-6}$ alkynyl, or cycloalkyl; any one of $R^2$, $R^3$, $R^4$, and $R^5$ represents $R^6R^7NSO_2NH$—$C_{1-6}$ alkyl where $R^6$ and $R^7$, which may be the same or different, represent a hydrogen atom or $C_{1-6}$ alkyl; and n is 0 or 1.

13 Claims, No Drawings

CEPHEM DERIVATIVES

This application is a 371 application of International Application No. PCT/JP97/04489 filed Dec. 8, 1997.

BACKGROUND OF THE INVENTION

1. Field of the Invention

The present invention relates to cephem antibiotics useful as pharmaceuticals for human beings and animals.

2. Background Art

Cephem antibiotics possesses excellent antimicrobial activity and low toxicity in mammals and hence are medicaments which are very useful for treatment of infectious diseases of mammals.

The so-called onium salt type cephem antibiotics typified by cefozopran and cefpirome, which have aminothiazolyl (aminothiadiazolyl) acetyl at the 7-position and a quaternary salt substituent at the 3-position, are characterized by having potent antimicrobial activity and a wide spectrum of bacteria from Gram-positive bacteria to Pseudomonas aeruginosa. Therefore, numerous studies and developments in the antibiotics of this type have been made in many countries in the world.

However, even the onium-salt-type cephem compounds, such as cefozopuran and cefpirome, are not always satisfactory in terms of antimicrobial activity against Pseudomonas aeruginosa or Gram-positive bacteria such as Staphylococcus aureus which have brought about a clinical problem in recent years. In addition, infectious diseases caused by methicillin-resistant Staphylococcus aureus (MRSA) or penicillin-resistant streptococcus pneumoniae (PRSP) have been a serious clinical problem these days. It is therefore strongly demanded to obtain novel onium salt type cephem antibiotics which have improved antimicrobial activity also against these bacteria (Chapter 11 by W. E. Wick, "Cephalosporins and Penicillins, Chemistry and Biology" edited by E. H. Flynn, Academic Press, New York, N.Y., 1972; 18.1 "Cephalosporins" by Hatsuo Aoki, "The Leading Studies in Antibiotics" edited by Masaji Ono and Satoshi Omura, Tokyo Kagaku Dojin Kabushiki Kaisha, Japan, 1987; and "Manifestation of Resistance and Molecular Genetics" by Ryoichi Okamoto and Matsuhisa Inoue, "Sogo Rinsho", vol. 42, No. 2, 1993).

In recent years, cephem derivatives having both quaternary ammonium methyl at the 3-position of the cephem ring and 2-(2-aminothiazol-4-yl)- or 2-(5-amino-1,2,4-thiadiazol-3-yl)-2-hydroxy(or substituted hydroxy) iminoacetamide group at the 7-position have been found to possess high antimicrobial activity and stability against β-lactamase, and numerous studies and developments on these cephem derivatives have been made in the art. Among others, cephem compounds having substituted or unsubstituted imidazo[5,1-b]thiazolium-6-yl at the 3-position of the cephem ring are described in WO 95/07912.

However, no compounds having sulfamidoalkyl or substituted sulfamidoalkyl on the imidazo[5,1-b]thiazole ring have been reported so far as the present inventors know.

SUMMARY OF THE INVENTION

The present inventors have now succeeded in synthesizing a novel cephem derivative having (substituted or unsubstituted sulfamido)alkylimidazo[5,1-b]thiazolium-6-yl at the 3-position. Furthermore, they have also found that this novel cephem derivative possesses potent antimicrobial activity against a wide spectrum of bacteria from Gram-positive bacteria to Gram-negative bacteria and, in addition, possesses high antimicrobial activity also against various β-lactamase-producing bacteria and significant antimicrobial activity against methicillin-resistant Staphylococcus aureus (MRSA), penicillin-resistant streptococcus pneumoniae (PRSP), and imipenem-resistant Pseudomonas aeruginosa. The present invention has been made based on such finding.

Accordingly, an object of the present invention is to provide a novel onium salt type cephem antibiotic which possesses potent antimicrobial activity against a wide spectrum of bacteria from Gram-negative bacteria to Pseudomonas aeruginosa and improved antimicrobial activity against various resistant bacteria such as methicillin-resistant Staphylococcus aureus (MRSA) and penicillin-resistant streptococcus pneumoniae (PRSP).

Thus, according to one aspect of the present invention, there is provided a cephem derivative represented by the formula (I) or a pharmaceutically acceptable salt thereof:

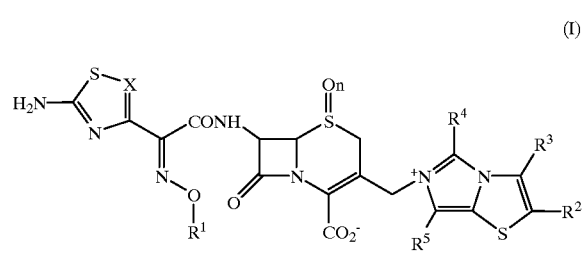

(I)

wherein
X represents CH or N;
R$^1$ represents a hydrogen atom,
C$_{1-6}$ alkyl in which one or more hydrogen atoms in the alkyl is optionally substituted by a halogen atom, a hydroxyl group, carboxyl, C$_{1-6}$ alkoxy-carbonyl, carbamoyl, N—C$_{1-6}$ alkylcarbamoyl, cyano, amino, or C$_{1-6}$ alkylamino,
C$_{2-6}$ alkenyl,
C$_{2-6}$ alkynyl, or
cycloalkyl;
any one of R$^2$, R$^3$, R$^4$, and R$^5$ represents R$^6$R$^7$NSO$_2$NH—C$_{1-6}$ alkyl where R$^6$ and R$^7$, which may be the same or different, represent a hydrogen atom or C$_{1-6}$ alkyl, and the other substituents of R$^2$, R$^3$, R$^4$, and R$^5$, which may be the same or different, each independently represents a hydrogen atom; C$_{1-6}$ alkoxy; C$_{1-6}$ alkylthio; cyano; carboxyl; C$_{1-6}$ alkoxy-carbonyl; carbamoyl; C$_{1-6}$ alkylcarbamoyl; formyl; amino; formylamino; acetylamino; methanesulfonylamino; a halogen atom; C$_{1-6}$ alkyl (in which one or more hydrogen atoms in the alkyl is optionally substituted by a hydroxyl group, C$_{1-6}$ alkoxy, mercapto, C$_{1-6}$ alkylthio, cyano, a halogen atom, carboxyl, C$_{1-6}$ alkoxy-carbonyl, carbamoyl, N—C$_{1-6}$ alkyl-carbamoyl, formyl, acetyl, acetoxy, hydroxyimino, C$_{1-6}$ alkoxyimino, amino, formylamino, acetylamino, trifluoroacetylamino, carbamoyloxy, N—C$_{1-6}$ alkyl-carbamoyloxy, methanesulfonylamino, ureido, N—C$_{1-6}$ alkylureido, C$_{1-6}$ alkoxycarbonylamino, or iminomethylamino); C$_{3-6}$ alkylene; C$_{3-6}$ cycloalkyl; C$_{2-6}$ alkenyl; or C$_{2-6}$ alkynyl,
or any two of R$^2$, R$^3$, R$^4$, and R$^5$ may combine with each other to represent C$_{1-6}$ alkylene, thereby forming a ring, one or more methylene groups in the alkylene being optionally substituted by NH, O, or S, the ring optionally having oxo (=O) as a substituent; and
n is 0 or 1.

DETAILED DESCRIPTION OF THE INVENTION

Definition

As used herein, the term "$C_{1-6}$ alkyl" as a group or a part of a group means any straight-chain or branched $C_{1-6}$ alkyl, preferably $C_{1-4}$ alkyl. The term "halogen" means a fluorine, chlorine, bromine, or iodine atom.

Compounds

In the formula (I), X represents CH or N, preferably N, and n is 0 or 1, preferably 0.

$R^1$ represents a hydrogen atom, $C_{1-6}$ alkyl, $C_{2-6}$ alkenyl (for example, 2-propenyl), $C_{2-6}$ alkynyl, or cycloalkyl (preferably $C_{3-7}$ cycloalkyl, for example, cyclopentyl).

One or more hydrogen atoms in the alkyl represented by $R^1$ is optionally substituted by a halogen atom, a hydroxyl group, carboxyl, $C_{1-6}$ alkoxy-carbonyl, carbamoyl, N—$C_{1-6}$ alkylcarbamoyl, cyano, amino, or $C_{1-6}$ alkylamino. A fluorine atom is preferred as the substituent. Substituted or unsubstituted alkyls represented by $R^1$ include methyl, ethyl, propyl, 1-methylethyl, fluoromethyl, difluoromethyl, 2-fluoroethyl, 3-fluoropropyl, 2-hydroxyethyl, cyanomethyl, (S)-1-carboxyethyl, carbamoylmethyl, and 1-carboxy-1-methylethyl.

According to a preferred embodiment of the present invention, $R^1$ preferably represents optionally substituted $C_{1-6}$ alkyl.

In the formula (I), any one of $R^2$, $R^3$, $R^4$, and $R^5$ represents $R^6R^7NSO_2NH$—$C_{1-6}$ alkyl wherein $R^6$ and $R^7$, which may be the same or different, represent a hydrogen atom or $C_{1-6}$ alkyl. Examples of $R^6R^7NSO_2NH$—$C_{1-6}$ alkyls include sulfamido $C_{1-6}$ alkyls (for example, sulfamidomethyl, sulfamidoethyl, (R)-1-(sulfamido)ethyl, and (S)-1-(sulfamido)ethyl), N—$C_{1-6}$ alkyl sulfamido $C_{1-6}$ alkyls (for example, (N-methylsulfamido)methyl), N'—$C_{1-6}$ alkyl sulfamido $C_{1-6}$ alkyls (for example, (N'-methylsulfamido)methyl), and N',N'-di-$C_{1-6}$ alkyl sulfamido $C_{1-6}$ alkyls (for example, (N',N'-dimethylsulfamido)methyl), and preferred examples thereof include sulfamido $C_{1-6}$ alkyl, N—$C_{1-6}$ alkyl sulfamido $C_{1-6}$ alkyls, N',N'-di-$C_{1-6}$ alkylsulfamido $C_{1-6}$ alkyl.

The other substituents of $R^2$, $R^3$, $R^4$, and $R^5$, which do not represent $R^6R^7NSO_2NH$—$C_{1-6}$ alkyl, may be the same or different and each independently represent a hydrogen atom; $C_{1-6}$ alkoxy; $C_{1-6}$ alkylthio (for example, methylthio); cyano; carboxyl; $C_{1-6}$ alkoxy-carbonyl (for example, ethoxycarbonyl); carbamoyl; $C_{1-6}$ alkyl-carbamoyl (for example, N-methylcarbamoyl); formyl; amino; formylamino; acetylamino; methanesulfonylamino; a halogen atom; substituted or unsubstituted $C_{1-6}$ alkyl; $C_{3-6}$ alkylene; $C_{3-6}$ cycloalkyl; $C_{2-6}$ alkenyl; or $C_{2-6}$ alkynyl. Substituents for the substituted $C_{1-6}$ alkyl include a hydroxyl group, $C_{1-6}$ alkoxy (for example, methoxy), mercapto, $C_{1-6}$ alkylthio, cyano, a halogen atom, carboxyl, $C_{1-6}$ alkoxy-carbonyl, carbamoyl, N—$C_{1-6}$ alkyl-carbamoyl, formyl, acetyl, acetoxy, hydroxyimino, $C_{1-6}$ alkoxyimino, amino, formylamino, acetylamino, trifluoroacetylamino, carbamoyloxy, N—$C_{1-6}$ alkyl-carbamoyloxy (for example, N-methylcarbamoyloxy), methanesulfonylamino, ureido, N—$C_{1-6}$ alkylureido (for example, N-methylureido), $C_{1-6}$ alkoxy-carbonylamino, and iminomethylamino. Two or more of these substituents may exist. Substituted or unsubstituted $C_{1-6}$ alkyls include, for example, methyl, ethyl, carboxymethyl, carbamoylmethyl, hydroxymethyl, hydroxyethyl, (formylamino)methyl, fluoromethyl, difluoromethyl, (hydroxyimino)methyl, dimethoxymethyl, acetoxymethyl, methoxymethyl, (R)-1-(formylamino)ethyl, (S)-1-(formylamino)ethyl, formylaminomethyl, (N-formyl-N-methylamino)methyl, ureidomethyl, (carbamoyloxy)methyl, (N-methylcarbamoyloxy)methyl, 2-(carbamoyloxy)ethyl, (acetylamino)methyl, (trifluoroacetylamino)methyl, (methanesulfonylamino)methyl, and (methanesulfonylamino)ethyl. According to a preferred embodiment of the present invention, at least one of the other substituents of $R^2$, $R^3$, $R^4$, and $R^5$, which do not represent $R^6R^7NSO_2NH$—$C_{1-6}$ alkyl, represents substituted alkyl.

Alternatively, any two of $R^2$, $R^3$, $R^4$, and $R^5$ may combine with each other to represent $C_{1-6}$ alkylene, thereby forming a ring. One or more methylene groups in the alkylene is optionally replaced by NH, O, or S, and the ring optionally has oxo (=O) as a substituent. According to a preferred embodiment of the present invention, specific examples thereof include a structure represented by the following formula (A) wherein $R^2$ together with $R^3$ represents alkylene having 3 carbon atoms and a structure represented by the following formula (B) wherein $R^3$ together with $R^4$ represents 1-oxo-2-azaalkylene:

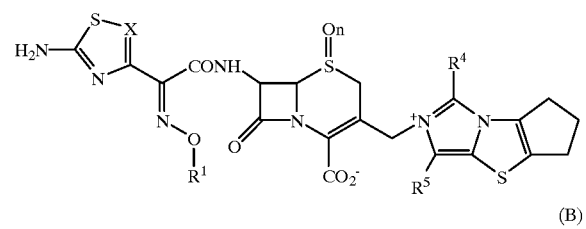

(A)

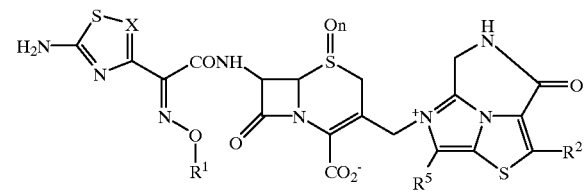

(B)

wherein X, $R^1$, $R^2$, $R^4$, $R^5$, and n are as defined above in the formula (I).

According to a preferred embodiment of the present invention, a preferred group of compounds of the present invention include those wherein X represents a nitrogen atom, $R^1$ represents halogen-substituted (preferably fluorine-substituted) or unsubstituted alkyl, and n is 0.

Another preferred group of compounds include those wherein all of $R^2$, $R^3$, $R^4$, and $R^5$, which do not represent $R^6R^7NSO_2NH$—$C_{1-6}$ alkyl, represent a hydrogen atom.

Still another preferred group of compounds include those wherein at least one of $R^2$, $R^3$, $R^4$, and $R^5$, which do not represent $R^6R^7NSO_2NH$—$C_{1-6}$ alkyl, represents $C_{1-6}$ alkyl with all the other substituents of $R^2$, $R^3$, $R^4$, and $R^5$ representing a hydrogen atom.

A further preferred group of compounds include those wherein $R^3$, $R^4$, or $R^5$ represents $R^6R^7NSO_2NH$—$C_{1-6}$ alkyl where both $R^6$ and $R^7$ represent a hydrogen atom, more preferably a group of compounds wherein $R^3$, $R^4$, or $R^5$, which does not represent $R^6R^7NSO_2NH$—$C_{1-6}$ alkyl, represents a hydrogen atom and $R^2$ represents a hydrogen atom.

A still further preferred group of compounds include those wherein $R^2$ represents $R^6R^7NSO_2NH$—$C_{1-6}$ alkyl (where both $R^6$ and $R^7$ represent $C_{1-6}$ alkyl), $R^3$ represents $C_{1-6}$ alkyl and $R^4$ and $R^5$ represent a hydrogen atom.

An additional preferred group of compounds include those wherein $R^4$ represents $R^6R^7NSO_2NH$—$C_{1-6}$ alkyl, where any one of $R^6$ and $R^7$ represents a hydrogen atom and the other substituent represents $C_{1-6}$ alkyl, or both $R^6$ and $R^7$ represent $C_{1-6}$ alkyl, more preferably a group of compounds wherein $R^2$, $R^3$, and $R^5$ represent a hydrogen atom.

The compounds represented by the formula (I) according to the present invention may be present in the form of a pharmaceutically acceptable salt. Salts usable herein include pharmaceutically acceptable nontoxic salts. Preferred examples of a salt formed at the amino group include salts of hydrohalogenic acids, such as hydrofluoric acid, hydrochloric acid, hydrobromic acid, and hydroiodic acid; salts of inorganic acids, such as sulfuric acid, nitric acid, phosphoric acid, perchloric acid, and carbonic acid; salts of carboxylic acids, such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, and malic acid; salts of acidic amino acids, such as aspartic acid and glutamic acid; and salts of organic acids, such as methanesulfonic acid and p-toluenesulfonic acid. Examples of salts formed at the carboxyl group include alkali metal salts, such as sodium, potassium, and lithium salts; alkaline earth metal salts, such as calcium and magnesium salts; ammonium salts; salts of organic amines, such as triethylamine, trimethylamine, diethylamine, pyridine, ethanolamine, triethanolamine, dicyclohexylamine, procaine, benzylamine, N-methylpiperidine, N-methylmorpholine, and diethylaniline; and salts of basic amino acids, such as lysine, arginine, and histidine.

Specific examples of compounds according to the present invention include:

1. (6R,7R)-7-[(Z)-2-(5-amino-1,2,4-thiadiazol-3-yl)-2-(fluoromethoxyimino)acetamido]-3-[3-sulfamidomethylimidazo[5,1-b]thiazolium-6-yl]methyl-3-cephem-4-carboxylate (inner salt);
2. (6R,7R)-7-[(Z)-2-(5-amino-1,2,4-thiadiazol-3-yl)-2-(2-fluoroethoxyimino)acetamido]-3-[3-sulfamidomethylimidazo[5,1-b]thiazolium-6-yl]methyl-3-cephem-4-carboxylate (inner salt);
3. (6R,7R)-7-[(Z)-2-(5-amino-1,2,4-thiadiazol-3-yl)-2-(fluoromethoxyimino)acetamido]-3-[3-sulfamidoethylimidazo[5,1-b]thiazolium-6-yl]methyl-3-cephem-4-carboxylate (inner salt);
4. (6R,7R)-7-[(Z)-2-(5-amino-1,2,4-thiadiazol-3-yl)-2-(fluoromethoxyimino)acetamido]-3-[5-sulfamidomethylimidazo[5,1-b]thiazolium-6-yl]methyl-3-cephem-4-carboxylate (inner salt);
5. (6R,7R)-7-[(Z)-2-(5-amino-1,2,4-thiadiazol-3-yl)-2-(methoxyimino)acetamido]-3-[5-sulfamidomethylimidazo[5,1-b]thiazolium-6-yl]methyl-3-cephem-4-carboxylate (inner salt);
6. (6R,7R)-7-[(Z)-2-(5-amino-1,2,4-thiadiazol-3-yl)-2-(ethoxyimino)acetamido]-3-[5-sulfamidomethylimidazo[5,1-b]thiazolium-6-yl]methyl-3-cephem-4-carboxylate (inner salt);
7. (6R,7R)-7-[(Z)-2-(5-amino-1,2,4-thiadiazol-3-yl)-2-(fluoromethoxyimino)acetamido]-3-[5-((R)-1-sulfamidoethyl)imidazo[5,1-b]thiazolium-6-yl]methyl-3-cephem-4-carboxylate (inner salt);
8. (6R,7R)-7-[(Z)-2-(5-amino-1,2,4-thiadiazol-3-yl)-2-(fluoromethoxyimino)acetamido]-3-[5-((S)-1-sulfamidoethyl)imidazo[5,1-b]thiazolium-6-yl]methyl-3-cephem-4-carboxylate (inner salt);
9. (6R,7R)-7-[(Z)-2-(5-amino-1,2,4-thiadiazol-3-yl)-2-(fluoromethoxyimino)acetamido]-3-[7-sulfamidomethylimidazo[5,1-b]thiazolium-6-yl]methyl-3-cephem-4-carboxylate (inner salt);
10. (6R,7R)-7-[(Z)-2-(5-amino-1,2,4-thiadiazol-3-yl)-2-(fluoromethoxyimino)acetamido]-3-[2-(N',N'-dimethylsulfamidomethyl)-3-methylimidazo[5,1-b]thiazolium-6-yl]methyl-3-cephem-4-carboxylate (inner salt);
11. (6R,7R)-7-[(Z)-2-(5-amino-1,2,4-thiadiazol-3-yl)-2-(fluoromethoxyimino)acetamido]-3-[5-((R)-1-N',N'-dimethylsulfamidoethyl)imidazo[5,1-b]thiazolium-6-yl)]methyl-3-cephem-4-carboxylate (inner salt); and
12. (6R,7R)-7-[(Z)-2-(5-amino-1,2,4-thiadiazol-3-yl)-2-(fluoromethoxyimino)acetamido]-3-[5-(N-methylsulfamidomethyl)imidazo[5,1-b]thiazolium-6-yl]methyl-3-cephem-4-carboxylate (inner salt).

The compounds represented by the formula (I) of the present invention have potent antimicrobial activity against a wide spectrum of bacteria from Gram-positive bacteria to Grame-negative bacteria including β-lactamase producing bacteria. In particular, it has higher antimicrobial activity against methicilline-resistant Staphylococcus aureus (MRSA), penicillin-resistant Streptococcus pneumoniae (PRSP), and imipenem-resistant Pseudomonas aeruginosa than the existing onium salt type cephem derivatives and hence is very useful as a therapeutic agent for infectious diseases derived from various pathogenic bacteria.

Preparation of compounds

Preferably, the compounds represented by the general formula (I) according to the present invention are prepared by a method represented by the following scheme:

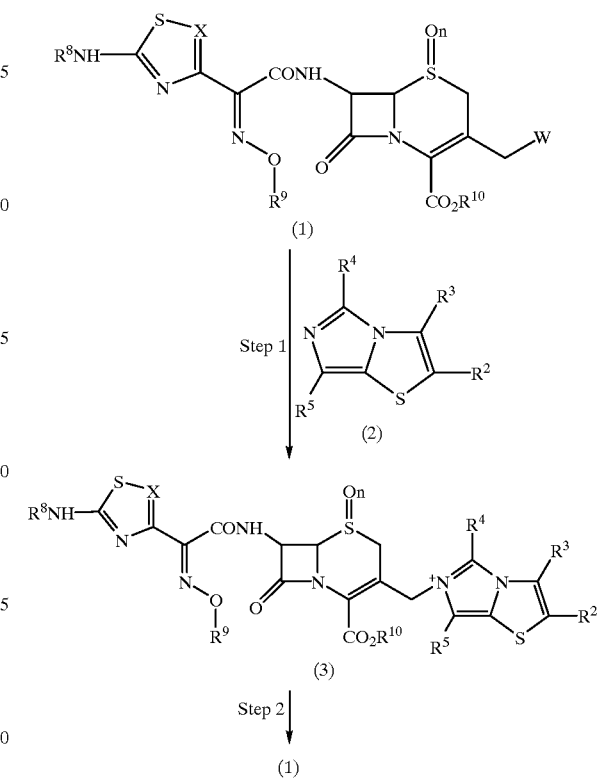

In the above reaction formula, X, $R^2$, $R^3$, $R^4$, $R^5$, and n are as defined above in the formula (I).

$R^8$ represents a hydrogen atom or an amino protective group, such as trityl, chloroacetyl, or formyl. $R^9$ may represent the same substituent as $R^1$, or alternatively may represent carboxyl protected by diphenylmethyl, benzyl, p-methoxybenzyl, p-nitrobenzyl, tert-butyl, allyl, or 2,2,2-trichloroethyl, or alternatively may represent a protective group for oxime such as trityl.

$R^{10}$ represents a hydrogen atom or an ester forming group as a carboxyl protective group, such as diphenylmethyl, benzyl, p-methoxybenzyl, p-nitrobenzyl, tert-butyl, allyl, or 2,2,2-trichloroethyl.

W represents a leaving group, such as a halogen atom (preferably a chlorine, bromine, or iodine atom), diphenylphosphoryloxy, methanesulfonyloxy, p-toluenesulfonyloxy, trifluoromethanesulfonyloxy, or acetoxy.

The compound (1) used in the step 1 may be produced by a conventional method described in WO 95/07912 or a method similar thereto. Substituted imidazo[5,1-b]thiazole (2) as the compound (2) may be produced by a conventional method described in WO 95/07912, WO 96/28455, or Japanese Patent Laid-Open No. 311071/1996 or a method similar thereto.

In the step 1, the compound (1) is reacted with at least one equivalent, preferably an excess amount, of the compound (2) in either an anhydrous organic solvent or a water-containing organic solvent to give the compound (3). Suitable organic solvents usable in the reaction include acetone, methyl ethyl ketone, ethyl acetate, chloroform, dichloromethane, tetrahydrofuran, dioxane, N,N-dimethylformamide, acetonitrile, hexamethylphosphoric triamide, toluene, methanol, and ethanol. The reaction temperature is preferably −20 to 50° C. After the completion of the reaction, the reaction solution is subjected to conventional post-treatment, and the compound (3) thus prepared is if necessary purified by silica gel or Sephadex LH-20 column chromatography or by crystallization.

When both $R^8$ and $R^{10}$ represent a hydrogen atom and $R^9$ and $R^1$ represent the same substituent, the compound represented by the formula (I) according to the present invention may be produced without carrying out the step 2.

On the other hand, when any one or two of or all of $R^8$, $R^9$, and $R^{10}$ represent a protective group, the protective group in the compound (3) may be removed in the step 2 to give the compound represented by the formula (I). The deprotection reaction may be carried out by a conventional method commonly used in the removal of a protective group, and the order of deprotection may be suitably determined. Specifically, when the deprotection may be carried out under acidic conditions, the compound (3) may be treated with trifluoroacetic acid, formic acid, hydrochloric acid or the like. On the other hand, when the deprotection may be carried out under reduction conditions, the compound (3) may be treated by catalytic reduction in the presence of various catalysts or with a metallic reducing agent, such as zinc. When $R^8$ represents chloroacetyl, the compound (3) may be reacted with various thioamides to remove this protective group.

The compound represented by the formula (I) thus prepared may be crystallized and precipitated by adjusting a solution containing the compound to suitable pH. If necessary, the compound may be isolated through purification by chromatography using a nonionic macroporous resin or by gel filtration using Sephadex or the like.

Use of compounds/pharmaceutical compositions

The compounds represented by the formula (I) according to the present invention have potent antimicrobial activity against a wide spectrum of bacteria from Gram-positive bacteria to Grame-negative bacteria including β-lactamase producing bacteria. In particular, it has higher antimicrobial activity against methicilline-resistant Staphylococcus aureus (MRSA), penicillin-resistant Streptococcus pneumoniae (PRSP), and imipenem-resistant Pseudomonas aeruginosa than the existing onium salt type cephem derivatives and hence is very useful as a therapeutic agent for infectious diseases derived from various pathogenic bacteria. Further, their toxicity is low, and their absorbability is high.

Therefore, the compounds of the present invention can be used for the treatment of infectious diseases, derived from various pathogenic bacteria, of animals including human beings.

A pharmaceutical composition comprising as an active ingredient a compound of the present invention or a pharmaceutically acceptable salt thereof can be administered either orally or parenterally (e.g. intravenous injection, intramuscular injection, subcutaneous administration, rectal administration, or percutaneous administration) to human beings or animals other than human beings.

Therefore, the pharmaceutical composition comprising as an active ingredient a compound of the present invention may be made into a preparation suitable for an administration route to be adopted. Specifically, it may be mainly made into any of the following preparations: an injection for intravenous or intramuscular injection; a capsule, a tablet, a granule, a powder, a pill, a subtilized granule or a troche for oral administration; a preparation for rectal administration; an oily suppository; and an aqueous suppository.

The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like which are commonly used in the art. Examples of the above additives which are nontoxic and employable in the preparations include lactose, fructos, glucose, starch, gelatin, magnesium carbonate, synthetic magnesium silicate, talc, magnesium stearate, methyl cellulose, or a salt thereof, gum arabic, polyethylene glycol, syrup, vaseline, glycerin, ethanol, propylene glycol, citric acid, sodium chloride, sodium sulfite and sodium phosphate.

The dosage of the compound of the present invention is properly determined in consideration of the regimen, the age and sex of a patient, and the conditions of diseases. However, for the treatment of infectious diseases, approximately 100 mg to 4000 mg, preferably 500 mg to 2000 mg of the compound is generally administered per day per adult individual at one time or several times.

EXAMPLES

Although the present invention will be described in more detail with reference to the following examples and test examples, it is not limited to these examples and test examples only.

Example 1

(6R,7R)-7-[(Z)-2-(5-Amino-1,2,4-thiadiazol-3-yl)-2-(fluoromethoxyimino)acetamido]-3-[3-sulfamidomethylimidazo[5,1-b]thiazolium-6-yl]methyl-3-cephem-4-carboxylate (inner salt)

Sodium iodide (90 mg) was added to a solution of 0.171 g of p-methoxybenzyl (6R,7R)-7-[(Z)-2-(5-amino-1,2,4-thiadiazol-3-yl)-2-(fluoromethoxyimino)acetamido]-3-chloromethyl-3-cephem-4-carboxylate in 1 ml of acetone in an argon atmosphere under ice cooling. The mixture was shielded from light and, in this state, was stirred for one hr.

Acetone was removed under reduced pressure. A 3:1 mixture (20 ml) of dichloromethane and ethyl acetate and 20 ml of water were added to the residue, followed by thorough stirring. The organic layer was separated, dried over anhydrous magnesium sulfate, and evaporated to dryness under reduced pressure. 3-Sulfamidomethylimidazo[5,1-b]thiazole (0.07 g) was added to a solution of the residue in 1 ml of dimethylformamide under ice cooling, and the mixture was shielded from light and, in this state, stirred at room temperature overnight. Ethyl acetate (10 ml) was added to the reaction solution under ice cooling, and the resultant precipitate was collected by filtration and dried. A 2 M aqueous sodium trifluoroacetate solution (15 ml) was added dropwise to a solution of the precipitate in 1 ml of dimethylformamide under ice cooling, and the resultant precipitate was collected by filtration and dried. Anisole (1 ml) was added to the precipitate, the mixture was thoroughly stirred, 3 ml of trifluoroacetic acid was added thereto under ice cooling, and the mixture was stirred for one hr. Cooled isopropyl ether (15 ml) was added to the reaction solution, and the resultant precipitate was collected by filtration and washed twice with 15 ml of isopropyl ether. The precipitate was then dried under reduced pressure and suspended in 10 ml of water, and the suspension was adjusted to pH 7.5 by addition of a saturated aqueous sodium hydrogencarbonate solution while elaborately stirring the suspension. The mixture was purified by column chromatography on 15 ml of Diaion HP-20 Resin (manufactured by Mitsubishi Chemical Corporation) (eluting solution: water 50 ml, 10–50% solution of methanol in 50 ml of water). A fraction containing the contemplated compound was evaporated to dryness. The residue was further purified by Sephadex LH-20 column (manufactured by Pharmacia Biotech) chromatography (50% solution of methanol in water) and octadecyl silica gel (manufactured by Nacalai Tesuque Inc.) chromatography (15% solution of methanol in water), concentrated under reduced pressure, and freeze-dried to give 0.055 g of the title compound.

NMR ($D_2O$) δ(HDO=4.70): 3.12, 3.55 (2H, dd, J=18.1 Hz), 4.43 (2H, s), 5.04, 5.21 (2H, dd, J=17.0 Hz), 5.17 (1H, d, J=5.0 Hz), 5.71 (2H, d, J=54.7 Hz), 5.77 (1H, d, J=5.0 Hz), 7.40 (1H, s), 7.70 (1H, s), 9.29 (1H, s)

Example 2

(6R,7R)-7-[(Z)-2-(5-Amino-1,2,4-thiadiazol-3-yl)-2-(2-fluoroethoxyimino)acetamido]-3-[3-sulfamidomethylimidazo[5,1-b]thiazolium-6-yl]methyl-3-cephem-4-carboxylate (inner salt)

In the same manner as in Example 1, 0.034 g of the title compound was prepared from 0.24 g of p-methoxybenzyl (6R,7R)-7-[(Z)-2-(5-amino-1,2,4-thiadiazol-3-yl)-2-(fluoroethoxyimino)acetamido]-3-chloromethyl-3-cephem-4-carboxylate, 0.07 g of 3-sulfamidoethylimidazo[5,1-b]thiazole, and 0.09 g of sodium iodide.

NMR ($D_2O$) δ(HDO=4.70): 3.13, 3.54 (2H, dd, J=17.9 Hz), 4.34–4.58 (4H, m), 4.44 (2H, s), 5.04, 5.21 (2H, dd, J=14.7 Hz), 5.17 (1H, d, J=4.8 Hz), 5.77 (1H, d, J=4.8 Hz), 7.41 (1H, s), 7.70 (1H, s)

Example 3

(6R,7R)-7-[(Z)-2-(5-Amino-1,2,4-thiadiazol-3-yl)-2-(fluoromethoxyimino)acetamido]-3-[3-sulfamidoethylimidazo[5,1-b]thiazolium-6-yl]methyl-3-cephem-4-carboxylate (inner salt)

In the same manner as in Example 1, 0.05 g of the title compound was prepared from 0.16 g of p-methoxybenzyl (6R,7R)-7-[(Z)-2-(5-amino-1,2,4-thiadiazol-3-yl)-2-(fluoromethoxyimino)acetamido]-3-chloromethyl-3-cephem-4-carboxylate, 0.07 g of 3-sulfamidoethylimidazo[5,1-b]thiazole, and 0.084 g of sodium iodide.

NMR ($D_2O$) δ(HDO=4.70): 3.04 (2H, t, J=6.1 Hz), 3.09, 3.50 (2H, dd, J=17.4 Hz), 5.02, 5.18 (2H, dd, J=14.0 Hz), 5.15 (1H, d, J=4.8 Hz), 5.70 (2H, d, J=54.3 Hz), 5.75 (1H, d, J=4.8 Hz), 7.18 (1H, s), 7.66 (1H, s) 9.32 (1H, s)

Example 4

(6R,7R)-7-[(Z)-2-(5-Amino-1,2,4-thiadiazol-3-yl)-2-(fluoromethoxyimino)acetamido]-3-[5-sulfamidomethylimidazo[5,1-b]thiazolium-6-yl]methyl-3-cephem-4-carboxylate (inner salt)

In the same manner as in Example 1, 0.036 g of the title compound was prepared from 0.108 g of p-methoxybenzyl (6R,7R)-7-[(Z)-2-(5-amino-1,2,4-thiadiazol-3-yl)-2-(fluoromethoxyimino)acetamido]-3-chloromethyl-3-cephem-4-carboxylate, 0.044 g of 5-sulfamidomethylimidazo[5,1-b]thiazole, and 0.057 g of sodium iodide.

NMR ($D_2O$) δ(HDO=4.70): 3.09, 3.44 (2H, dd, J=18.5 Hz), 4.81 (2H, s), 5.16 (1H, d, J=4.7 Hz), 5.20 (2H, s), 5.72 (2H, d, J=54.2 Hz), 5.77 (1H, d, J=4.7 Hz), 7.48 (1H, d, J=4.4 Hz), 7.66 (1H, s), 7.94 (1H, d, J=4.4 Hz)

Example 5

(6R,7R)-7-[(Z)-2-(5-Amino-1,2,4-thiadiazol-3-yl)-2-(methoxyimino)acetamido]-3-[5-sulfamidomethylimidazo[5,1-b]thiazolium-6-yl]methyl-3-cephem-4-carboxylate (inner salt)

5-Sulfamidomethylimidazo[5,1-b]thiazole (0.278 g) and 0.332 g of potassium iodide were added to a solution of 0.553 g of p-methoxybenzyl (6R,7R)-7-[(Z)-2-(5-amino-1,2,4-thiadiazol-3-yl)-2-(methoxyimino)acetamido]-3-chloromethyl-3-cephem-4-carboxylate in 2 ml of dimethylformamide under ice cooling, and the mixture was shielded from light and, in this state, stirred at room temperature overnight. The reaction solution was treated and purified in the same manner as in Example 1 to give 0.127 g of the title compound.

NMR ($D_2O$) δ(HDO=4.70): 3.09, 3.43 (2H, dd, J=17.7 Hz), 3.94 (3H, s), 4.80 (2H, s), 5.14 (1H, d, J=4.8 Hz), 5.20 (2H, s), 5.75 (1H, d, J=4.8 Hz), 7.47 (1H, d, J=4.4 Hz), 7.65 (1H, s), 7.93 (1H, d, J=4.4 Hz)

Example 6

(6R,7R)-7-[(Z)-2-(5-amino-1,2,4-thiadiazol-3-yl)-2-(ethoxyimino)acetamido]-3-[5-sulfamidomethylimidazo[5,1-b]thiazolium-6-yl]methyl-3-cephem-4-carboxylate (inner salt)

In the same manner as in Example 1, 0.032 g of the title compound was prepared from 0.155 g of p-methoxybenzyl (6R,7R)-7-[(Z)-2-(5-amino-1,2,4-thiadiazol-3-yl)-2-(ethoxyimino)acetamido]-3-chloromethyl-3-cephem-4-carboxylate, 0.07 g of 5-sulfamidomethylimidazo[5,1-b]thiazole, and 0.082 g of sodium iodide.

NMR ($D_2O$) δ(HDO=4.70): 1.27 (3H, t, J=7.0 Hz), 3.18, 3.49 (2H, dd, J=18.1 Hz), 4.27 (2H, q, J=7.0 Hz), 4.83 (2H, s), 5.18 (1H, d, J=4.8 Hz), 5.27 (2H, s), 5.81 (1H, d, J=4.8 Hz), 7.60 (1H, d, J=4.3 Hz), 7.79 (1H, s), 8.04 (1H, d, J=4.3 Hz)

Example 7

(6R,7R)-7-[(Z)-2-(5-Amino-1,2,4-thiadiazol-3-yl)-2-(fluoromethoxyimino)acetamido]-3-[5-((R)-1-sulfamidoethyl)imidazo[5,1-b]thiazolium-6-yl]methyl-3-cephem-4-carboxylate (inner salt)

In the same manner as in Example 1, 0.033 g of the title compound was prepared from 0.171 g of p-methoxybenzyl (6R,7R)-7-[(Z)-2-(5-amino-1,2,4-thiadiazol-3-yl)-2-(fluoromethoxyimino)acetamido]-3-chloromethyl-3-cephem-4-carboxylate, 0.081 g of 5-((R)-1-sulfamidoethyl)imidazo[5,1-b]thiazole, and 0.09 g of sodium iodide.

NMR (DMSO-$d_6$) δ: 1.55 (3H, d, J=7.1 Hz), 3.15, 3.37 (2H, dd, J=17.4 Hz), 4.98 (1H, d, J=5.0 Hz), 5.19, 5.60 (2H, dd, J=14.2 Hz), 5.32–5.36 (1H, m), 5.64–5.69 (1H, m), 5.76 (2H, d, J=54.4 Hz), 7.15 (2H, br-s), 7.80 (1H, d, J=4.3 Hz), 7.87 (1H, br-s), 8.07 (1H, s), 8.22 (2H, br-s), 8.25 (1H, d, J=4.3 Hz), 9.72 (1H, d, J=8.2 Hz)

Example 8

(6R,7R)-7-[(Z)-2-(5-Amino-1,2,4-thiadiazol-3-yl)-2-(fluoromethoxyimino)acetamido]-3-[5-((S)-1-sulfamidoethyl)imidazo[5,1-b]thiazolium-6-yl]methyl-3-cephem-4-carboxylate (inner salt)

In the same manner as in Example 1, 0.029 g of the title compound was prepared from 0.171 g of p-methoxybenzyl (6R,7R)-7-[(Z)-2-(5-amino-1,2,4-thiadiazol-3-yl)-2-(fluoromethoxyimino)acetamido]-3-chloromethyl-3-cephem-4-carboxylate, 0.08 g of 5-((S)-1-sulfamidoethyl)imidazo[5,1-b]thiazole, and 0.09 g of sodium iodide.

NMR ($D_2O$) δ(HDO=4.70): 1.57 (2H, d, J=7.1 Hz), 3.10, 3.39 (2H, dd, J=17.7 Hz), 5.17 (1H, d, J=4.8 Hz), 5.22, 5.31 (2H, dd, J=15.3 Hz), 5.36 (1H, q, J=7.4 Hz), 5.73 (2H, d, J=54.5 Hz), 5.78 (1H, d, J=4.8 Hz), 7.51 (1H, d, J=4.3 Hz), 7.63 (1H, s), 8.05 (1H, d, J=4.3 Hz)

Example 9

(6R,7R)-7-[(Z)-2-(5-Amino-1,2,4-thiadiazol-3-yl)-2-(fluoromethoxyimino)acetamido]-3-[7-sulfamidomethylimidazo[5,1-b]thiazolium-6-yl]methyl-3-cephem-4-carboxylate (inner salt)

In the same manner as in Example 1, 0.034 g of the title compound was prepared from 0.098 g of p-methoxybenzyl (6R,7R)-7-[(Z)-2-(5-amino-1,2,4-thiadiazol-3-yl)-2-(fluoromethoxyimino)acetamido]-3-chloromethyl-3-cephem-4-carboxylate, 0.04 g of 7-sulfamidomethylimidazo[5,1-b]thiazole, and 0.052 g of sodium iodide.

NMR ($D_2O$) δ(HDO=4.70): 3.12, 3.43 (2H, dd, J=18.0 Hz), 4.45 (2H, s), 5.17 (1H, d, J=4.8 Hz), 5.18 (2H, s), 5.72 (2H, d, J=55.2 Hz), 5.77 (1H, d, J=4.8 Hz), 7.42 (1H, d, J=4.0 Hz), 7.78 (1H, d, J=4.0 Hz)

Example 10

(6R,7R)-7-[(Z)-2-(5-amino-1,2,4-thiadiazol-3-yl)-2-(fluoromethoxyimino)acetamido]-3-[2-(N',N'-dimethylsulfamidomethyl)-3-methylimidazo[5,1-b]thiazolium-6-yl]methyl-3-cephem-4-carboxylate (inner salt)

In the same manner as in Example 1, 0.059 g of the title compound was prepared from 0.114 g of p-methoxybenzyl (6R,7R)-7-[(Z)-2-(5-amino-1,2,4-thiadiazol-3-yl)-2-(fluoromethoxyimino)acetamido]-3-chloromethyl-3-cephem-4-carboxylate, 0.053 g of 2-(N',N'-dimethylsulfamidomethyl)-3-methylimidazo[5,1-b]thiazole, and 0.06 g of sodium iodide.

NMR ($D_2O$) δ(HDO=4.70): 2.36 (3H, s), 2.68 (6H, s), 3.11, 3.54 (2H, dd, J=17.7 Hz), 4.30 (2H, s), 5.00, 5.19 (2H, dd, J=14.8 Hz), 5.16 (1H, d, J=4.7 Hz), 5.71 (2H, d, J=54.7 Hz), 5.80 (1H, d, J=4.7 Hz), 7.64 (1H, s), 9.22 (1H, s)

Example 11

(6R,7R)-7-[(Z)-2-(5-Amino-1,2,4-thiadiazol-3-yl)-2-(fluoromethoxyimino)acetamido]-3-[5-((R)-1-N',N'-dimethylsulfamidoethyl)imidazo[5,1-b]thiazolium-6-yl)]methyl-3-cephem-4-carboxylate (inner salt)

In the same manner as in Example 1, 0.049 g of the title compound was prepared from 0.171 g of p-methoxybenzyl (6R,7R)-7-[(Z)-2-(5-amino-1,2,4-thiadiazol-3-yl)-2-(fluoromethoxyimino)acetamido]-3-chloromethyl-3-cephem-4-carboxylate, 0.099 g of 5-((R)-1-N',N'-dimethylsulfamidoethyl)imidazo[5,1-b]thiazole, and 0.09 g of sodium iodide.

NMR ($D_2O$) δ(HDO=4.70): 1.56 (3H, d, J=7.4 Hz), 2.62 (6H, s), 3.08, 3.40 (2H, dd, J=18.0 Hz), 5.14 (1H, d, J=5.0 Hz), 5.28–5.30 (3H, m), 5.71 (2H, d, J=54.2H z), 5.76 (1H, d, J=5.0 Hz), 7.53 (1H, d, J=4.2 Hz), 7.65 (1H, s), 8.03 (1H, d, J=4.2 Hz)

Example 12

(6R,7R)-7-[(Z)-2-(5-Amino-1,2,4-thiadiazol-3-yl)-2-(fluoromethoxyimino)acetamido]-3-[5-(N-methylsulfamidomethyl)imidazo[5,1-b]thiazolium-6-yl]methyl-3-cephem-4-carboxylate (inner salt)

a) 2 g of 5-sulfamidomethylimidazo[5,1-b]thiazole was dissolved in 20 ml of a 1:1 mixed solution of dimethylformamide and acetonitrile, 2.5 g of silver oxide and 1.0 ml of methyl iodide were added to the solution, the mixture was stirred at 0 to 5° C. for one hr and then at room temperature for one hr. The reaction solution was filtered, concentrated under reduced pressure, and purified on Sephadex LH-20 to give 0.615 g of 5-(N-methylsulfamidomethyl)imidazo[5,1-b]thiazole.

b) In the same manner as in Example 1, 0.037 g of the title compound was prepared from 0.171 g of p-methoxybenzyl (6R,7R)-7-[(Z)-2-(5-amino-1,2,4-thiadiazol-3-yl)-2-(fluoromethoxyimino)acetamido]-3-chloromethyl-3-cephem-4-carboxylate, 0.102 g of 5-(N-methylsulfamidomethyl)imidazo[5,1-b]thiazole, and 0.09 g of sodium iodide.

NMR ($D_2O$) δ(HDO=4.70): 2.76 (3H, s), 3.03, 3.38 (2H, dd, J=18.5 Hz), 4.78 (2H, s), 5.07 (1H, d, J=4.7 Hz), 5.18 (2H, s), 5.67 (2H, d, J=54.2 Hz), 5.71 (1H, d, J=4.7 Hz), 7.45 (1H, d, J=4.4 Hz), 7.64 (1H, s), 7.87 (1H, d, J=4.4 Hz)

The structures of the respective compounds prepared in the above examples are summarized below.

| Example | R₁ | Side chain at 3-position |
|---|---|---|
| 1 | CH₂F |  |
| 2 | CH₂CH₂F | |
| 3 | CH₂F |  |
| 4 | CH₂F |  |
| 5 | CH₃ | |
| 6 | C₂H₅ | |
| 7 | CH₂F |  |
| 8 | CH₂F |  |
| 9 | CH₂F |  |
| 10 | CH₂F |  |
| 11 | CH₂F |  |
| 12 | CH₂F |  |

Biological Test

The antibacterial activity of the compounds according to the present invention was assayed in terms of the minimum inhibitory concentration, for various bacteria, measured by the conventional two-fold dilution method described in, for example, CHEMOTHERAPY, Vol. 29, No. 1, 76–79 (1981). The measurement was carried out in the following manner: $10^6$ CFU/ml of a bacterium to be tested was inoculated on a Medium N for disc susceptibility test (manufactured by Nissui Pharmaceutical Co., Ltd.) and cultivated at 35° C. for 18 to 20 hr.

The test compounds were the compounds prepared in Examples 4 and 5, Cefozopran (CZOP, control 1), Cefpirome (CPR, control 2), the compound prepared in Example 66 (control 3) described in WO 95/07912. The measurements of the minimum inhibitory concentration (μg/ml) are summarized in Table 1.

TABLE 1

| | Minimum Inhibitory Concentration (μg/ml) | | | | |
|---|---|---|---|---|---|
| Test Strain | Ex. 4 | Ex. 5 | Control 1 | Control 2 | Control 3 |
| S. aureus 209P JC-1 | 0.78 | 0.78 | 0.39 | 0.20 | 0.78 |
| S. aureus 126*¹ | 6.25 | 6.25 | 50 | 50 | 6.25 |
| S. epidermidis ATCC14990 | 0.78 | 0.78 | 0.78 | 0.39 | 1.56 |
| S. pneumoniae IP692 | ≦0.025 | ≦0.025 | 0.05 | ≦0.025 | ≦0.025 |
| S. pneumoniae PRC9*² | 0.39 | 0.39 | 1.56 | 0.78 | 0.39 |
| S. pneumoniae JPR9*² | 0.20 | — | — | — | 0.78 |
| S. pneumoniae JPR20*² | 0.05 | — | — | — | 0.39 |
| E. coli NIHJ JC-2 | ≦0.025 | 0.05 | 0.05 | 0.05 | ≦0.025 |
| K. pneumoniae PCI602 | ≦0.025 | 0.05 | 0.10 | 0.05 | ≦0.025 |
| M. morganii 1510/S-1 | ≦0.025 | 0.05 | 0.10 | ≦0.025 | ≦0.025 |
| C. freundii GN346/16 | ≦0.025 | 0.05 | 0.05 | 0.05 | ≦0.025 |
| E. cloacae G-0008 | 0.05 | 0.10 | 0.10 | 0.05 | 0.05 |
| S. marcescens No. 1 | 0.05 | 0.10 | 0.10 | ≦0.025 | 0.05 |
| P. aeruginosa GN10362 | 0.39 | 0.78 | 0.78 | 3.13 | 0.78 |
| P. aeruginosa E-2 | 0.78 | 0.78 | 0.78 | 3.13 | 1.56 |
| P. aeruginosa PA01*³ | 3.13 | 3.13 | 12.5 | 25 | 3.13 |

Note)
*¹Methicilline-resistant *Staphylococcus aureus* (MRSA)
*²Penicillin-resistant *Streptococcus pneumoniae* (PRSP)
*³Imipenem- and Aztreonam-resistant *Pseudomonas aeruginosa*

Preparation
Preparation for Injection

A compound according to the present invention is aseptically charged into vials so that each vial contains 1000 mg (potency) of the compound of the invention.

| Capsulated preparation | |
|---|---|
| Compound of the invention | 250 parts (potency) |
| Milk sugar | 60 parts (potency) |
| Magnesium stearate | 5 parts (potency) |

The ingredients are homogeneously mixed, and the mixture is charged into capsules so that each capsule contains 250 mg (potency) of the compound of the invention.

| Soft capsulated preparation for rectal administration | |
|---|---|
| Olive oil | 160 parts |
| Polyoxyethylene lauryl ether | 10 parts |
| Sodium hexametaphosphate | 5 parts |

25 parts (potency) of the compound of the present invention is added to and homogeneously mixed with a base comprising the above ingredients, and the mixture is charged into soft capsules for rectal administration so that each capsule may contain 250 mg (potency) of the compound of the invention.

What is claimed is:

1. A cephem derivative represented by the formula (I) or a pharmaceutically acceptable salt thereof:

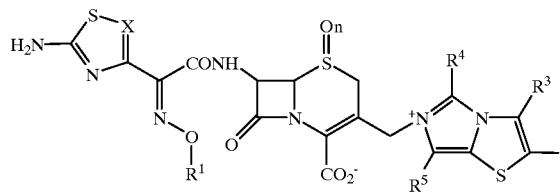

wherein

X represents CH or N;

$R^1$ represents a hydrogen atom, $C_{1-6}$ alkyl in which one or more hydrogen atoms in the alkyl is optionally substituted by a halogen atom, a hydroxyl group, carboxyl, $C_{1-6}$ alkoxy-carbonyl, carbamoyl, N—$C_{1-6}$ alkylcarbamoyl, cyano, amino, or $C_{1-6}$ alkylamino, $C_{2-6}$ alkenyl, $C_{2-6}$ alkynyl, or cycloalkyl;

any one of $R^2$, $R^3$, $R^4$, and $R^5$ represents $R^6R^7NSO_2NH$—$C_{1-6}$ alkyl where $R^6$ and $R^7$, which may be the same or different, represent a hydrogen atom or $C_{1-6}$ alkyl, and the other substituents of $R^2$, $R^3$, $R^4$, and $R^5$, which may be the same or different, each independently represents a hydrogen atom; $C_{1-6}$ alkoxy; $C_{1-6}$ alkylthio; cyano; carboxyl; $C_{1-6}$ alkoxy-carbonyl; carbamoyl; $C_{1-6}$ alkyl-carbamoyl; formyl; amino; formylamino; acetylamino; methanesulfonylamino; a halogen atom; $C_{1-6}$ alkyl (in which one or more hydrogen atoms in the alkyl is optionally substituted by a hydroxyl group, $C_{1-6}$ alkoxy, mercapto, $C_{1-6}$ alkylthio, cyano, a halogen atom, carboxyl, $C_{1-6}$ alkoxy-carbonyl, carbamoyl, N—$C_{1-6}$ alkyl-carbamoyl, formyl, acetyl, acetoxy, hydroxyimino, $C_{1-6}$ alkoxyimino, amino, formylamino, acetylamino, trifluoroacetylamino, carbamoyloxy, N—$C_{1-6}$ alkyl-carbamoyloxy, methanesulfonylamino, ureido, N—$C_{1-6}$ alkylureido, $C_{1-6}$ alkoxycarbonylamino, or iminomethylamino) $C_{3-6}$ cycloalkyl; $C_{2-6}$ alkenyl; or $C_{2-6}$ alkynyl, or any two of $R^2$, $R^3$, $R^4$, and $R^5$ may combine with each other to represent $C_{1-6}$ alkylene, thereby forming a ring, one or more methylene groups in the alkylene being optionally replaced by NH, O, or S, the ring optionally having oxo (=O) as a substituent; and n is 0 or 1.

2. The compound or pharmaceutically acceptable salt thereof according to claim 1, wherein X represents a nitrogen atom, $R^1$ represents halogen-substituted or unsubstituted alkyl and n is 0.

3. The compound or pharmaceutically acceptable salt thereof according to claim 2, wherein the halogen atom is a fluorine atom.

4. The compound or pharmaceutically acceptable salt thereof according to any one of claims 1 to 3, wherein all of $R^2$, $R^3$, $R^4$, and $R^5$, which do not represent $R^6R^7NSO_2NH$—$C_{1-6}$ alkyl, represent a hydrogen atom.

5. The compound or pharmaceutically acceptable salt thereof according to any one of claims 1 to 3, wherein at least one of $R^2$, $R^3$, $R^4$, and $R^5$, which do not represent $R^6R^7NSO_2NH$—$C_{1-6}$ alkyl, represents $C_{1-6}$ alkyl and all the other substituents of $R^2$, $R^3$, $R^4$, and $R^5$ represent a hydrogen atom.

6. The compound or pharmaceutically acceptable salt thereof according to any one of claims 1 to 3, wherein $R^3$, $R^4$, or $R^5$ represents $R^6R^7NSO_2NH$—$C_{1-6}$ alkyl (where both $R^6$ and $R^7$ represent a hydrogen atom).

7. The compound or pharmaceutically acceptable salt thereof according to claim 6, wherein $R^3$, $R^4$, or $R^5$, which does not represent $R^6R^7NSO_2NH$—$C_{1-6}$ alkyl (where both $R^6$ and $R^7$ represent a hydrogen atom), represents a hydrogen atom, and $R^2$ represents a hydrogen atom.

8. The compound or pharmaceutically acceptable salt thereof according to any one of claims 1 to 3, wherein $R^2$ represents $R^6R^7NSO_2NH$—$C_{1-6}$ alkyl(where both $R^6$ and $R^7$ represent $C_{1-6}$ alkyl), $R^3$ represents $C_{1-6}$ alkyl and $R^4$ and $R^5$ represent a hydrogen atom.

9. The compound or pharmaceutically acceptable salt thereof according to any one of claims 1 to 3, wherein $R^4$ represents $R^6R^7NSO_2NH$—$C_{1-6}$ alkyl (where any one of $R^6$ and $R^7$ represents a hydrogen atom and the other substituent represents $C_{1-6}$ alkyl, or both $R^6$ and $R^7$ represent $C_{1-6}$ alkyl).

10. The compound or pharmaceutically acceptable salt thereof according to claim 9, wherein $R^2$, $R^3$, and $R^5$ represent a hydrogen atom.

11. A pharmaceutical composition comprising a compound according to any one of claims 1 to 3 together with a pharmaceutically acceptable carrier.

12. A method for treating infectious diseases, comprising administering a compound according to any one of claims 1 to 3 to a mammal.

13. The method according to claim 12, wherein the mammal is a human being.

* * * * *